(12) United States Patent
Tan et al.

(10) Patent No.: US 10,595,791 B2
(45) Date of Patent: Mar. 24, 2020

(54) ENDOVASCULAR HEAT EXCHANGE SYSTEMS AND METHODS WITH BLOOD FLOW MONITORING AND NOTIFICATION FUNCTIONS

(71) Applicant: ZOLL Circulation, Inc., San Jose, CA (US)

(72) Inventors: Qing Tan, Somerville, MA (US); Gary A Freeman, Waltham, MA (US)

(73) Assignee: ZOLL Circulation, Inc., San Jose, CA (US)

(*) Notice: Subject to any disclaimer, the term of this patent is extended or adjusted under 35 U.S.C. 154(b) by 715 days.

(21) Appl. No.: 14/639,816

(22) Filed: Mar. 5, 2015

(65) Prior Publication Data
US 2015/0272513 A1   Oct. 1, 2015

Related U.S. Application Data

(60) Provisional application No. 61/949,822, filed on Mar. 7, 2014.

(51) Int. Cl.
  *A61B 5/026*   (2006.01)
  *A61B 5/01*   (2006.01)
  (Continued)

(52) U.S. Cl.
  CPC .......... *A61B 5/7282* (2013.01); *A61B 5/026* (2013.01); *A61F 7/12* (2013.01); *A61B 5/01* (2013.01);
  (Continued)

(58) Field of Classification Search
  CPC .......... A61B 5/01; A61B 5/026; A61B 5/028; A61B 5/7282; A61B 5/0261;
  (Continued)

(56) References Cited

U.S. PATENT DOCUMENTS

| 5,217,019 A | 6/1993 | Hughes |
| 5,443,072 A * | 8/1995 | Kagan ............... A61B 5/021 |
| | | 600/500 |

(Continued)

FOREIGN PATENT DOCUMENTS

| EP | 0862379 A1 | 9/1998 |
| JP | 2013507193 A | 3/2013 |

(Continued)

OTHER PUBLICATIONS

PCT International Search Report dated Sep. 2, 2015 in related PCT Application No. PCT/US2015/018998.

(Continued)

*Primary Examiner* — Navin Natnithithadha
(74) *Attorney, Agent, or Firm* — Fish & Richardson P.C.

(57) ABSTRACT

Endovascular heat exchange systems and methods wherein a heat exchange catheter is positionable within the vasculature of a patent to exchange heat with the patient's flowing blood. The rate at which heat is being exchanged is determined and quantitative blood flow determinations may be made based on the rate of heat exchange. The system provides notification(s) to personnel when one or more blood flow-related events occur(s), such as a) resumption or continuation of effective spontaneous circulation; b) cessation of absence of effective spontaneous circulation, c) the occurrence of spontaneous or cardiac-compression-generated circulation that is below a minimum effective blood flow rate and e) the occurrence of spontaneous or cardiac-compression-generated circulation that is at or above a minimum effective blood flow rate.

25 Claims, 3 Drawing Sheets

(51) Int. Cl.
*A61F 7/12* (2006.01)
*A61B 5/00* (2006.01)

(52) U.S. Cl.
CPC ............. *A61B 5/742* (2013.01); *A61B 5/7405* (2013.01); *A61B 5/746* (2013.01); *A61F 2007/126* (2013.01)

(58) Field of Classification Search
CPC ..... A61B 5/0265; A61B 5/027; A61B 5/0275; A61B 5/0278; A61F 7/12
See application file for complete search history.

(56) References Cited

U.S. PATENT DOCUMENTS

| | | | |
|---|---|---|---|
| 5,486,208 A | 1/1996 | Ginsburg | |
| 5,531,776 A * | 7/1996 | Ward | A61N 1/0517 |
| | | | 128/898 |
| 5,716,386 A * | 2/1998 | Ward | A61B 17/12022 |
| | | | 606/27 |
| 6,149,670 A * | 11/2000 | Worthen | A61F 7/12 |
| | | | 607/104 |
| 6,296,654 B1 * | 10/2001 | Ward | A61B 17/12 |
| | | | 128/898 |
| 6,299,583 B1 | 10/2001 | Eggers et al. | |
| 6,610,083 B2 | 8/2003 | Keller et al. | |
| 6,620,188 B1 | 9/2003 | Ginsburg et al. | |
| 6,673,098 B1 | 1/2004 | Machold et al. | |
| 6,702,840 B2 | 3/2004 | Keller et al. | |
| 6,752,786 B2 | 6/2004 | Callister | |
| 7,087,026 B2 | 8/2006 | Callister et al. | |
| 7,632,235 B1 | 12/2009 | Karicherla et al. | |
| 7,806,915 B2 | 10/2010 | Scott et al. | |
| 9,198,826 B2 * | 12/2015 | Banville | A61H 31/004 |
| 2002/0173731 A1 | 11/2002 | Martin et al. | |
| 2003/0060723 A1 * | 3/2003 | Joo | A61B 5/0535 |
| | | | 600/510 |
| 2003/0225336 A1 * | 12/2003 | Callister | A61B 5/029 |
| | | | 600/505 |
| 2004/0267324 A1 | 12/2004 | Geheb et al. | |
| 2005/0054939 A1 * | 3/2005 | Ben-Ari | A61B 5/0261 |
| | | | 600/506 |
| 2007/0043409 A1 | 2/2007 | Brian et al. | |
| 2008/0249388 A1 * | 10/2008 | Kumhyr | A61B 5/00 |
| | | | 600/368 |
| 2009/0043366 A1 | 2/2009 | Dae | |
| 2012/0016279 A1 | 1/2012 | Banville et al. | |
| 2012/0325426 A1 | 12/2012 | Noda et al. | |
| 2013/0090593 A1 | 4/2013 | Dabrowiak | |
| 2013/0150929 A1 * | 6/2013 | Machold | A61M 25/10 |
| | | | 607/105 |
| 2013/0178923 A1 | 7/2013 | Dabrowiak | |
| 2013/0324873 A1 | 12/2013 | Babaeizadeh et al. | |
| 2015/0164417 A1 * | 6/2015 | Tupin, Jr. | A61B 5/0205 |
| | | | 600/407 |

FOREIGN PATENT DOCUMENTS

| | | |
|---|---|---|
| WO | WO 2010/002352 A1 | 1/2010 |
| WO | WO2011/044408 A3 | 4/2011 |

OTHER PUBLICATIONS

Extended European Search Report dated Oct. 20, 2017 in related European Application No. 15757951.7.
Office Action dated Jan. 22, 2019 in corresponding Japanese Patent Application No. 2016-556009.

* cited by examiner

ENDOVASCULAR HEAT EXCHANGE SYSTEMS AND METHODS WITH BLOOD FLOW MONITORING AND NOTIFICATION FUNCTIONS

RELATED APPLICATION

This application claims priority to U.S. Provisional Patent Application No. 61/949,822 entitled Endovascular Heat Exchange Systems And Methods With Blood Flow Monitoring And Notification Functions filed Mar. 7, 2014, the entire disclosure of which is expressly incorporated herein by reference.

FIELD OF THE INVENTION

The present invention relates generally to the fields of biology, medicine and biomedical engineering and more particularly to endovascular heat exchange devices and their use in human or animal subjects to determine a) when cardiac arrest (CA) has occurred and/or b) when or post-arrest return of spontaneous circulation (ROSC) has occurred and/or c) whether ongoing cardiopulmonary resuscitation (CPR) efforts are producing at least minimally effective blood flow (MEBF) through the subject's vasculature.

BACKGROUND OF THE INVENTION

Pursuant to 37 CFR 1.71(e), this patent document contains material which is subject to copyright protection and the owner of this patent document reserves all copyright rights whatsoever.

Cardiac Arrest (CA) is essentially a loss of effective cardiac activity. CA typically occurs as the result of a nonperfusing cardiac arrhythmia. The most common nonperfusing cardiac arrhythmias are ventricular fibrillation, pulseless ventricular tachycardia, pulseless electrical activity, asystole and pulseless bradycardia.

Typically, in the absence of a verifiable do-not-resuscitate order, CPR should be performed on any subject who becomes unconscious and is found to be pulseless. CPR typically consists of the administration of cardiac compressions in combination with artificial ventilation to maintain at least MEBF and oxygenation during cardiac arrest. The cardiac compressions may be administered manually and/or by way of a cardiac compression device such as the AutoPulse® Noninvasive Cardiac Support Pump (ZOLL Circulation, Sunnyvalle, Calif.).

CPR cardiac compressions are typically initiated as soon as possible after the subject becomes pulseless and are continued until either ROSC has been established or death is pronounced. In some cases, ROSC may occur before spontaneous or fully effective respiration has occurred. Thus, it is not uncommon for a subject to remain intubated and on ventilation support even after ROSC has occurred and cardiac compressions have been stopped.

Some CA subjects in whom ROSC is successfully restored may subsequently undergo repeat CA, thereby necessitating recommencement of cardiac compressions and further continuance of CPR until either ROSC has once again occurred or death is pronounced.

The ability to determine precisely when CA or ROSC has occurred is desirable to enable rescuers treating the subject to know when to start or stop administering cardiac compressions. Additionally, while CPR is ongoing, it is desirable have some feedback as to how much endovascular blood flow is actually being created by the cardiac compressions so that rescuers may know whether the cardiac compressions are being administered with sufficient force and in a manner that is creating at least MEBF.

In clinical settings where a CA subject is intubated and on ventilation support, a respiratory monitoring technique known as quantitative waveform capnography has been used to determine the occurrence of ROSC as well as to assess whether cardiac compressions are being performed in a manner that attains at least MEBF. Typically, quantitative waveform capnography involves the use of a device known as a capnograph to continuously measure a ventilation parameter known as end-tidal carbon dioxide or $ETCO_2$ (sometimes alternatively referred to as $PetCO_2$). $ETCO_2$ is a direct measurement of ventilation in the lungs. It is also useable as an indirect indicator of blood circulation (i.e., a decrease in circulatory perfusion decreases the rate at which carbon dioxide is exhaled through the lungs thereby decreasing $ETCO_2$. $ETCO_2$ in an adult patient with normal spontaneous circulation is around 35-45 mmHg. In an intubated CA subject who is undergoing CPR, an $ETCO_2$ of less than 10 mmHg may be an indication that MEBF has not achieved and that the manner in which the cardiac compressions are being applied may require some modification.

When effective cardiac compressions are given during CA, the $ETCO_2$ value is expected to be 10-20 mmHg. When ROSC occurs, the $ETCO_2$ then increases to 35-45 mmHg. Thus, in an intubated patient cardiac arrest patient, quantitative waveform capnography has been suggested as a tool for monitoring the effectiveness of CPR cardiac compressions and determining when ROSC occurs. However, in order to perform quantitative waveform capnography the patient typically must be intubated and connected to a capnography device that is programmed to monitor $ETCO_2$.

Today, many critically ill patients are treated with Endovascular Temperature Management (ETM). In ETM, a heat exchange catheter is inserted into the patient's vasculature and connected to a console which generally includes a programmable controller, heater, cooler, pumping apparatus and user interface. A desired target temperature may be input, via the user interface, and the controller will then cause heated or cooled heat exchange fluid to be circulated through the heat exchange catheter. The exchange of heat between the circulated heat exchange fluid and the patient's blood flowing past the heat exchange catheter causes the patient's core body temperature to be raised or lowered to the target temperature. The ETM system will then maintain the patient's body temperature at or near the target temperature until the patient is returned to normothermia and the ETM treatment is discontinued. Such ETM systems are currently available from ZOLL Circulation, Inc., Sunnyvale, Calif. and Phillips-Innercool, San Diego, Calif.

In addition to being useable for controlling the patient's body temperature, ETM systems can also be programmed to compute the patient's blood flow rate based on the rate at which heat is exchanged between the heat exchange fluid and the patient's blood. Essentially, the faster the blood flow rate the greater the rate of heat exchange and vice versa. Details as to the manner in which ETM systems may be used to determine blood flow rate are described in U.S. Pat. No. 7,087,026 (Callister, et al.) entitled Devices and Methods for Measuring Blood Flow Rate or Cardiac Output and for Heating or Cooling the Body, the entire disclosure of which is expressly incorporated herein by reference.

It would be advantageous if heat exchange catheters and associated control equipment used for ETM could be additionally modified to provide real time indications of noteworthy blood-flow events such as the occurrence of cardiac or circulatory arrest and/or whether cardiac compressions being administered during CPR are effective to create MEBF and/or when ROSC has occurred.

SUMMARY OF THE INVENTION

The present invention provides endovascular heat exchange systems and methods useable to modify and/or maintain a patient's body temperature using a heat exchange catheter positioned within the patient's vasculature, while additionally providing information or alerts to caregivers or other personnel upon the occurrence of a noteworthy change in blood flow rate, such as a) resumption or continuation of effective spontaneous circulation; b) cessation or absence of effective spontaneous circulation, c) the occurrence of spontaneous or cardiac-compression-generated circulation that is below a minimum effective blood flow rate and/or e) the occurrence of spontaneous or cardiac-compression-generated circulation that is at or above a minimum effective blood flow rate.

In accordance the present invention, the rate of heat exchange occurring between the indwelling heat exchange catheter and the patient's body may be used as an indicator of when ROSC occurs following a CA. In embodiments where a temperature-controlled heat exchange fluid is circulated through the heat exchange catheter, the rate of heat being exchanged between the heat exchange catheter and the patient's body may be calculated using the temperature of the heat exchange fluid flowing into the heat exchange catheter, the temperature of the heat exchange fluid flowing out of the heat exchange catheter and the flow rate of the heat exchange fluid. Sensors may be provided on heat exchange fluid inflow and outflow lines to sense and communicate these data to a controller. The controller is programmed to use such data to calculate the rate of heat exchange by a suitable formula, such as the following:

$$q = m \cdot (t_{in} - t_{out}) K$$

wherein q=heat exchange, m=flow rate of heat exchange fluid, $t_{in}$=temperature of heat exchange fluid entering the heat exchange catheter, $t_{out}$=temperature of heat exchange fluid exiting the heat exchange catheter and K=the thermal constant of the heat exchange fluid being used (e.g., 0.9% saline solution).

In some embodiments of the invention, the rate of heat exchange may be used as a basis for distinguishing between quantitative blood flow rates in the patient and providing notification when noteworthy changes in blood flow occur, such as a) the return (or continuation) of ROSC; b) cessation of absence of ROSC, c) the occurrence of spontaneous or cardiac-compression-generated circulation that is below a minimum effective blood flow (MEBF) rate and d) the occurrence of spontaneous or cardiac-compression-generated circulation that is at or above MEBF. In some embodiments of the invention, the method may be carried out using an automated system wherein a controller is programmed to calculate the heat exchange rate and/or blood flow rate based on heat exchange and to issue, through a visual, audio or other suitable apparatus, a notification of when noteworthy changes in blood flow have occurred.

Further in accordance with the present invention, there is provided an automated heat exchange catheter system comprising: a) a heat exchange catheter having a heat exchange surface that is insertable into the subject's vasculature; b) a programmable controller; c) apparatus for circulating heat exchange fluid through the heat exchange catheter while inserted in the subject's vasculature such heat will be exchanged across the heat exchange surface between heat exchange fluid being circulated through the heat exchange catheter and blood that flows through the subject's vasculature in heat exchange proximity to the heat exchange surface and d) one or more sensors for measuring the rate at which heat is being exchanged between heat exchange fluid being circulated through the heat exchange catheter and blood flowing through the subject's vasculature in heat exchange proximity to the heat exchange surface. In this system, the controller receives signals from the sensor(s) and is programmed to use those received signals to determine the occurrence of at least one event selected from; a) resumption or continuation of effective spontaneous circulation; b) cessation of absence of effective spontaneous circulation, c) the occurrence of spontaneous or cardiac-compression-generated circulation that is below a minimum effective blood flow (MEBF) rate and d) the occurrence of spontaneous or cardiac-compression-generated circulation that is at or above a minimum effective blood flow rate. In this system, the rate at which blood is flowing through the patient's vasculature may be determined on the basis of the rate at which heat is being exchanged, using the following formula:

$$\text{blood flow rate} = (\text{temp1} - \text{temp2}) * A / \text{delta\_time}$$

where temp1 is the average temperature of the heat exchange fluid coming out of the heat exchange catheter; temp2 is the average temperature of the heat exchange fluid going into the heat exchange catheter body; A is a constant depending on the property of the fluid and delta_time is a short period of time for averaging purposes. Alternative formulas may also be used where appropriate.

Further in accordance with the present invention, there is provided a modification package for modifying an existing endovascular temperature management system of the above-summarized character to additionally perform the functions of monitoring blood flow rate and providing information or alerts to caregivers or other personnel upon the occurrence of a noteworthy change in blood flow rate, such as a) resumption or continuation of effective spontaneous circulation; b) cessation or absence of effective spontaneous circulation, c) the occurrence of spontaneous or cardiac-compression-generated circulation that is below a minimum effective blood flow rate and/or e) the occurrence of spontaneous or cardiac-compression-generated circulation that is at or above a minimum effective blood flow rate. Such modification package may comprises executable code stored on a storage medium and deliverable to the controller of the endovascular temperature management system to determine blood flow rate based on the rate at which heat is being exchanged between the heat exchange catheter and the patient's blood and to determine, on that basis, the occurrence of at least one event selected from; a) resumption or continuation of effective spontaneous circulation; b) cessation of absence of effective spontaneous circulation, c) the occurrence of spontaneous or cardiac-compression-generated circulation that is below a minimum effective blood flow rate and e) the occurrence of spontaneous or cardiac-compression-generated circulation that is at or above a minimum effective blood flow rate. In some embodiments, the modification package may additionally program the controller to cause an existing display or other user interface component of the system to display or otherwise provide an indication or notification (e.g., alarm) when the event has occurred. In other embodiments, the modification package may include an add-on notification apparatus, such as display or audible alarm hardware, that is connectable to the system and which receives signals from the controller to provides the desired indication or notification (e.g., alarm) when the event has occurred.

Still further in accordance with the invention, there is provided method for providing notification to a patient's caregiver or other personnel of at least one patient-related event selected from a) resumption or continuation of effective spontaneous circulation; b) cessation of absence of effective spontaneous circulation, c) the occurrence of spontaneous or cardiac-compression-generated circulation that is below a minimum effective blood flow rate and e) the occurrence of spontaneous or cardiac-compression-generated circulation that is at or above a minimum effective blood flow rate.

Such method generally comprises the steps of 1) obtaining or providing a system which comprises i) a heat exchange catheter having a heat exchange surface that is insertable into the subject's vasculature; ii) a programmable controller; iii) apparatus for circulating heat exchange fluid through the heat exchange catheter while inserted in the subject's vasculature such heat will be exchanged across the heat exchange surface between heat exchange fluid being circulated through the heat exchange catheter and blood that flows through the subject's vasculature in heat exchange proximity to the heat exchange surface and iv) one or more sensors for measuring the rate at which heat is being exchanged between heat exchange fluid being circulated through the heat exchange catheter and blood flowing through the subject's vasculature in heat exchange proximity to the heat exchange surface, wherein the controller receives signals from said at least one sensor and is programmed to use those received signals to determine the occurrence of at least one event selected from; a) resumption or continuation of effective spontaneous circulation; b) cessation of absence of effective spontaneous circulation, c) the occurrence of spontaneous or cardiac-compression-generated circulation that is below a minimum effective blood flow rate and e) the occurrence of spontaneous or cardiac-compression-generated circulation that is at or above a minimum effective blood flow rate; 2) inserting the heat exchange catheter into the subject's vasculature; 3) using the system to warm or cool blood flowing through the subject's vasculature, thereby resulting in warming or cooling of all or a portion of the subject's body and d) additionally using the system to provide notification to a patient's caregiver or other personnel of at least one event selected from; a) resumption or continuation of effective spontaneous circulation; b) cessation of absence of effective spontaneous circulation, c) the occurrence of spontaneous or cardiac-compression-generated circulation that is below a minimum effective blood flow rate and e) the occurrence of spontaneous or cardiac-compression-generated circulation that is at or above a minimum effective blood flow rate.

Still further aspects and details of the present invention will be understood upon reading of the detailed description and examples set forth herebelow.

BRIEF DESCRIPTION OF THE DRAWINGS

The following detailed description and examples are provided for the purpose of non-exhaustively describing some, but not necessarily all, examples or embodiments of the invention, and shall not limit the scope of the invention in any way.

DETAILED DESCRIPTION OF THE INVENTION

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

Figure 1:
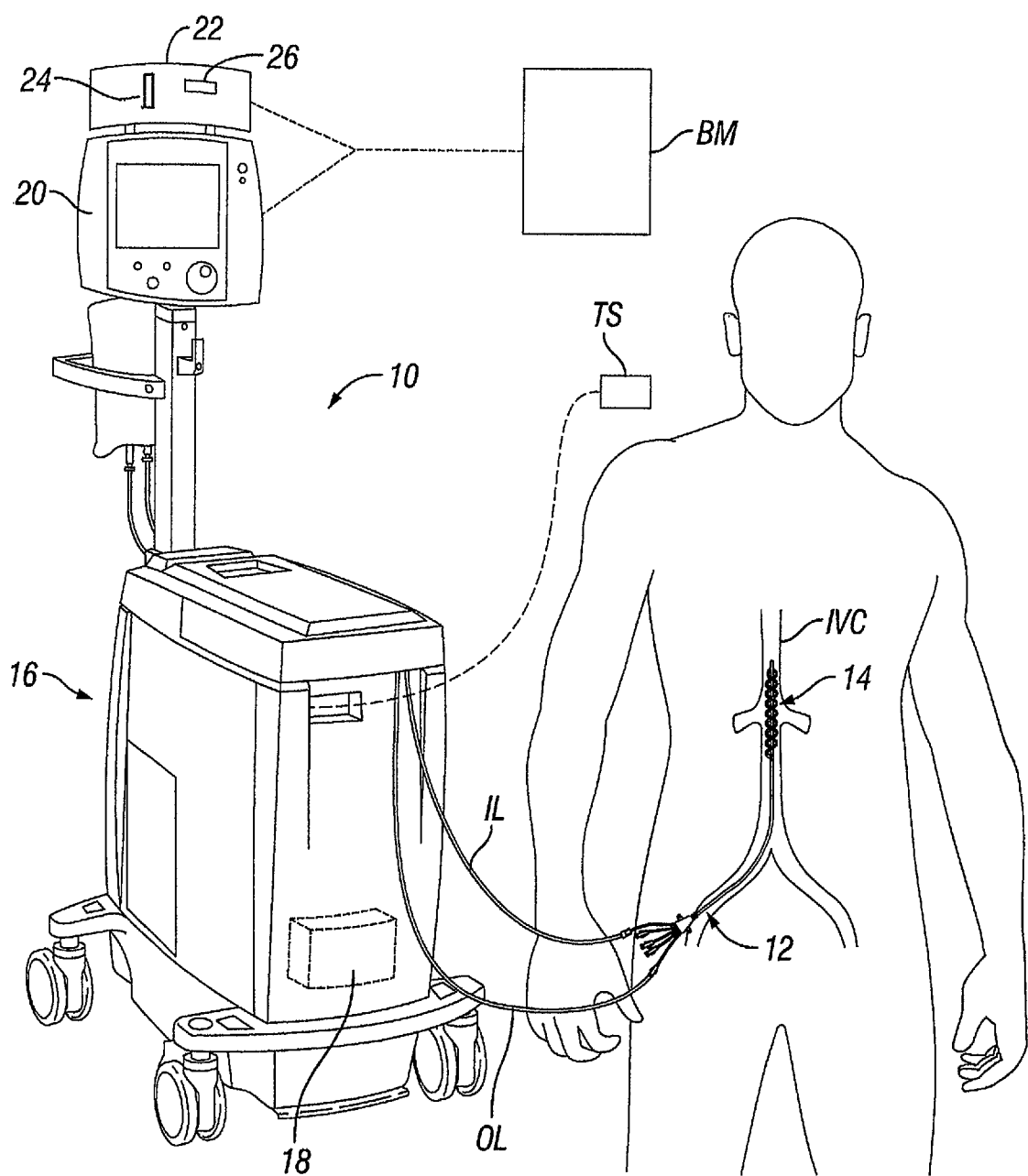
FIG. 1 is a schematic diagram of one non-limiting example of an ETM system according to the present invention.

FIG. 1 shows an example of an ETM system 10 of the present invention. This ETM system 10 generally comprises a heat exchange catheter 12 and a console 16. The heat exchange catheter 12 has a heat exchange region 14 that is positionable within the vasculature of a patient. In the particular example shown, the heat exchange catheter 12 is inserted via a femoral vein and advanced to a position where the heat exchange region 14 is within the inferior vena cava IVC.

The console 16 includes a display/user interface 20, a programmable controller 18 and various other pumping and temperature control apparatus for circulating temperature-controlled heat exchange fluid through the heat exchange catheter 12 such that heat will exchange, via the heat exchange region 14, between the controlled-temperature heat exchange fluid being circulated through the heat exchange region and blood flowing past the heat exchange region 14 through the patient's IVC. This ETM system is a closed-loop system. Heat exchange fluid is circulated from the console 16, through inflow line IL, through an inflow lumen of the catheter, through the heat exchange region 14, then through an outflow lumen of the catheter 12, through the outflow line OL and back into the console 16. The system is equipped with sensors which monitor the temperature of heat exchange fluid flowing into the inflow line IL and out of the outflow line OL. These monitored ingoing and outcoming heat exchange fluid temperatures are transmitted to the controller 18.

This ETM system also includes at least one body temperature sensor TS that may be placed at a desired location on or in the patient's body to monitor the patient's body temperature and to transmit the monitored body temperature to the controller 18. The patient's caregiver or other personnel may input a desired target body temperature via the display/user interface 20 and the controller 18 then controls operation of the pumping and/or temperature control components of the system 10 to modify the temperature and/or flow rate of heat exchange fluid being circulated through the catheter 12 to raise or lower the monitored body temperature to be substantially the same as the input target body temperature and to thereafter maintain that target body temperature for a desired period of time. Specific examples of ETM systems of this general type are described in U.S. Pat. No. 5,486,208 (Ginsburg); U.S. Pat. No. 6,610,083 (Keller at al.); U.S. Pat. No. 6,620,188 (Ginsburg, at al.); U.S. Pat. No. 6,673,098 (Machold et al.); U.S. Pat. No. 6,702,840 (Keller et al.); U.S. Pat. No. 6,752,786 (Callister); U.S. Pat. No. 7,806,915 (Scott et al.) as well as U.S. Patent Application Publication Nos. 2007/0043409 (Brian); 2012/0325426 (Noda et al.); 2013/0178923 (Dabrowiak); 2013/0090780 (Dabrowiak at al.) and 2013/0090593 (Dabrowiak et al.), the entire disclosures of which are expressly incorporated herein by reference. Additionally, ETM systems of this general type are commercially available as the Thermogard XF™ Temperature Management System (ZOLL Circulation, Inc., Sunnyvale, Calif.) and the Philips InnerCool RTx™ Endovascular System (Phillips Healthcare, Andover, Mass.).

In accordance with the present invention, the controller 18 of this ETM system 10 is additionally programmed to use the monitored outgoing and incoming heat exchange fluid temperatures and/or computed heat exchange rate (q) as described above, to determine the occurrence of at least one event selected from; a) resumption or continuation of effective spontaneous circulation; b) cessation of absence of effective spontaneous circulation, c) the occurrence of spontaneous or cardiac-compression-generated circulation that is below a minimum effective blood flow rate and e) the occurrence of spontaneous or cardiac-compression-generated circulation that is at or above a minimum effective blood flow rate. Indicia of the controller-determined blood flow rate and/or notifications (e.g., visual or auditory alarms) indicating the occurrence of the event(s) may, in some embodiments, be provided through the existing display/user interface 20. Alternatively, an add-on notification apparatus 24 may be connected to the system in the manner shown in the example of FIG. 1. In either event, the system 10 will provide an indication of current blood flow rate and/or an indication of when one or more of the event(s) have occurred. In the particular non-limiting shown in FIG. 1, the system 10 includes both a blood flow indicator 24 which indicates the current controller-determined blood flow rate and an alarm 26 which emits a visual and/or audible alarm when one or more specific blood-flow related event(s) occurs, such as; a) resumption or continuation of effective spontaneous circulation; b) cessation of absence of effective spontaneous circulation, c) the occurrence of spontaneous or cardiac-compression-generated circulation that is below a minimum effective blood flow rate and a) the occurrence of spontaneous or cardiac-compression-generated circulation that is at or above a minimum effective blood flow rate.

The blood flow indicator 24 and alarm 26 may comprises any suitable types of apparatus. In one non-limiting example, the blood flow indicator may be a graphic display, such as a moving column or bar graph marked with graduations to indicate MEBF as well as a range associated with spontaneous circulation (e.g., 4 to 7 liters per minute). Also, in one non-limiting example, the alarm 26 could be one or more light sources, such as light emitting diode(s), which emit different colors of light to indicate different alarm states.

For example, a green light may indicate normal blood flow as expected in a patient with a beating heart and spontaneous circulation, a red light may indicate a cessation of blood flow as would occur during cardiac or circulatory arrest without administration of CPR cardiac compressions, an amber light may indicate the presence of some blood flow but less than MEBF (such as would occur in a cardiac arrest patient who is receiving cardiac compressions that are insufficient to provide MEBF) and a blue light may the presence of some blood flow at or above MEBF but below the spontaneous circulation range (such as would occur in a cardiac arrest patient who is receiving cardiac compressions that are sufficient to provide MEBF but in whom ROSC has not yet occurred). Optionally, different audible alarm tones may be emitted along with each visual alarm state. In some embodiments, the system 10 may be connected to a bedside monitor BM so that the monitored blood flow rate and/or alarms may be displayed or emitted from the bedside monitor BM as well as any central or unit monitoring station(s) in communication with the bedside monitor.

FIG. 1 shows a hypothetical, non-limiting example of a basic method of the present invention in a patient who in a patient who is being treated with an endovascular temperature management system 10. After the patient has suffered CA, a baseline determination of heat exchange rate (q) is made, preferably without ongoing CPR chest compressions. To accomplish this, a user may trigger the controller 18 to store or note the baseline heat exchange rate at the desired time during CA, such as by pushing a button or entering a code on the display/user interface 20. After a baseline CA heat exchange rate has been stored or noted by the controller 18, the controller 18 will make continuous or periodic determinations of the heat exchange rate (q), if and when the heat exchange rate (q) changes by an amount deemed to be indicative of ROSC (e.g., an increase of approximately 40% over CA baseline), the controller 18 will then issue a notification to the patient's caregivers, such as visual and/or auditory alarm. Upon receiving such ROSC alarm, the caregivers may take clinical measures indicated by the occurrence of ROSC, such as discontinuation of CPR chest compressions.

Figure 2:
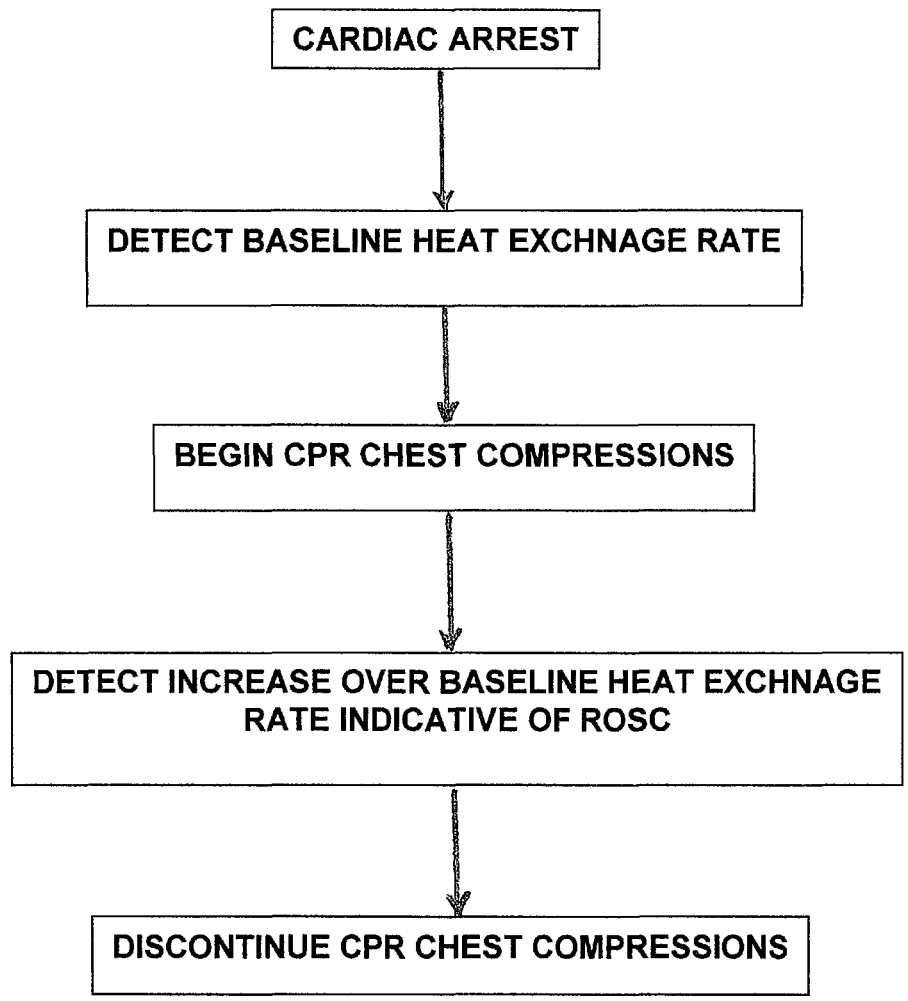
FIG. 2 is a flow diagram showing one non-limiting example of a method of the present invention in which a change in the rate of heat exchange between an indwelling heat exchange catheter and the patient's body is used as an indication of ROSC following CA in the patient.
Figure 3:
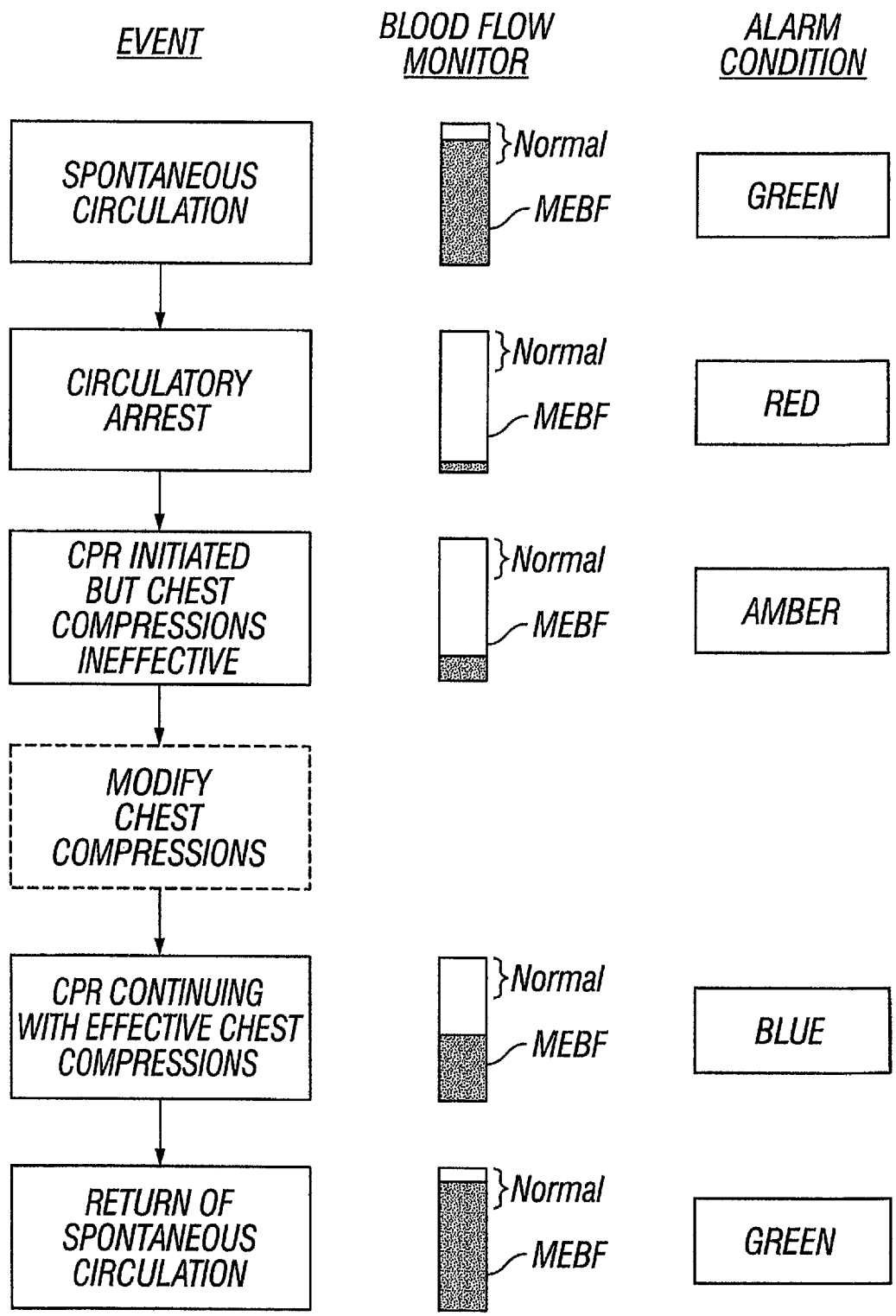
FIG. 3 is a flow diagram showing another non-limiting example of a method in which the present invention is utilized in a patient who undergoes CA, then CPR with sub-effective cardiac compressions, then CPR with effective cardiac compressions followed by successful ROSC.

FIG. 2 is a flow diagram showing another hypothetical, non-limiting example of a method of the present invention. In this method, more complex quantitative determinations are made to differentiate between and provide notification of different blood flow states in a critically ill patient who is being treated with an endovascular temperature management system 10 of the present invention. As seen in FIG. 2, while the patient's heart is beating normally and normal spontaneous circulation is ongoing, the controller 18 will determine based on the heat exchange rate that the patient's endovascular blood flow rate is within a normal range and an alarm 26 will emit a green light or other indicator of normal blood flow rate. Thereafter, when the patient suffers CA, the blood flow monitor 24 will indicate that endovascular blood flow has substantially ceased and the alarm 26 will emit a red light or other indication of CA. Thereafter, if CPR is initiated but the cardiac compressions are being ineffectively administered, the blood flow monitor 24 will indicate a blood flow level below MEBF and the alarm 26 will emit an amber light or other indicator of sub-MEBF blood flow. Upon noting the amber light or other amber light or other indicator of sub-MEBF blood flow, caregivers may modify the manner in which the cardiac compressions are being administered so that they become more effective, which will then cause the blood flow monitor 24 to indicate CPR-induced blood flow at or above MEBF but less than that which is associated with spontaneous circulation. Thereafter, when ROSC occurs, the blood flow monitor 24 will again indicate that the patient's endovascular blood flow is in the normal range and the alarm 26 will again emit a green light or other indicator that ROSC has occurred. Upon observing such green light or other indicator that ROSC has occurred, caregivers may then take appropriate clinical measures, such as discontinuation of CPR cardiac compressions.

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the substantial absence of other elements, steps, members, components, compositions, reactants, parts or portions unless otherwise noted. AH reasonable additions, deletions, modifications and alterations are to be considered equivalents of the described examples and embodiments and are to be included within the scope of the following claims.

What is claimed is:

1. A system comprising:
a heat exchange catheter having a heat exchange surface that is insertable into subject's vasculature;
a programmable controller;
apparatus for circulating heat exchange fluid through the heat exchange catheter while inserted in the subject's vasculature such that heat will be exchanged across the heat exchange surface between heat exchange fluid being circulated through the heat exchange catheter and blood that flows through the subject's vasculature in heat exchange proximity to the heat exchange surface;
one or more sensors for measuring a rate at which heat is being exchanged between heat exchange fluid being circulated through the heat exchange catheter and blood flowing through the subject's vasculature in heat exchange proximity to the heat exchange surface; and
wherein the controller receives signals from said one or more sensors and is programmed to use those received signals to determine a rate, if any, at which heat is being exchanged across the heat exchange surface and to ascertain whether the determined rate, if any, is indicative of an occurrence of at least one event selected from: a) resumption or continuation of effective spontaneous circulation; b) cessation or of absence of effective spontaneous circulation, c) the occurrence of spontaneous or cardiac-compression-generated circulation that is below a minimum effective blood flow rate and d) the occurrence of spontaneous or cardiac-compression-generated circulation that is at or above a minimum effective blood flow rate;
wherein, when the system is being used in a subject who lacks effective spontaneous circulation and is receiving cardiac compressions, the system determines the rate, if any, at which heat is being exchanged across the heat exchange surface while cardiac compressions are ongoing and determines, while the cardiac compressions are ongoing, when the determined rate, if any, is indicative of a resumption or continuation of effective spontaneous circulation.

2. A system according to claim 1 further comprising notification apparatus to notify a caregiver or other medical personnel of the occurrence of said at least one event.

3. A system according to claim 2 wherein the notification apparatus comprises a visible display.

4. A system according to claim 2 wherein the notification apparatus comprises an audible alarm.

5. A system according to claim 2 wherein the notification apparatus comprises a visible display and an audible alarm.

6. A system according to claim 3 wherein the visible display comprises a variable indicator that shows real time variation in blood flow rate.

7. A system according to claim 3 wherein the visible display comprises a visual indicator of when said at least one event is occurring.

8. A system according to claim 7 wherein the visual indicator comprises one or more light emitters.

9. A system according to claim 2 wherein the notification apparatus provides a) a first notification indicating the resumption or continuation of effective spontaneous circulation; b) a second notification indicating the cessation or absence of effective spontaneous circulation, c) a third notification indicating when spontaneous or cardiac-compression-generated circulation is occurring but is failing to generate minimum effective blood flow and d) a fourth notification indicating when spontaneous or cardiac-compression-generated circulation is occurring and is generating at least minimum effective blood flow.

10. A system according to claim 9 wherein the first notification comprises a light of a first color, the second notification comprises a light of a second color, the third notification comprises a light of a third color and the fourth notification comprises a light of a fourth color.

11. A system according to claim 10 wherein at least the second and third notifications are accompanied by audible alarms.

12. A modification package for modifying an existing endovascular temperature management system which comprises: a) apparatus for recirculating heat exchange fluid through a heat exchange catheter that is positionable within a subject's vasculature such that heat will be exchanged, across a heat exchange surface of the catheter, between heat exchange fluid being circulated through the heat exchange catheter and blood that flows through the subject's vasculature in heat exchange proximity to the heat exchange surface, b) a programmable controller programmed to control operation of the system so as to adjust or maintain a desired subject body temperature and c) sensors useable for measuring the temperature of heat exchange fluid entering the catheter and the temperature of heat exchange fluid exiting the catheter and to generate signals based on those measured temperatures;
wherein, the modification package comprises executable code stored on a storage medium and deliverable to the controller to program the controller to use signals received from said sensors to determine the occurrence of at least one event selected from; resumption or continuation of effective spontaneous circulation; cessation or absence of effective spontaneous circulation, the occurrence of spontaneous or cardiac-compression-generated circulation that is below a minimum effective blood flow rate; and the occurrence of spontaneous or cardiac-compression generated circulation that is at or above a minimum effective blood flow rate;
wherein the executable code programs the controller such that, when the endovascular temperature management system is being used in a subject who lacks effective spontaneous circulation and is receiving cardiac compressions, the controller uses said signals received from said sensors to determine, while the cardiac compressions are ongoing, when a resumption of effective spontaneous circulation occurs.

13. A modification package according to claim 12 wherein the code further programs the controller to issue notification signals to a notification apparatus which notifies personnel of the occurrence of said at least one event.

14. A modification package according to claim 13 wherein the existing endovascular temperature management system includes an existing notification apparatus that performs other functions and wherein the code causes the controller to send notification signals to the existing notification apparatus so that the existing notification apparatus notifies personnel of the occurrence of said at least one event in addition to performance of its other functions.

15. A modification package according to claim 14 wherein the existing notification apparatus comprises a liquid crystal display.

16. A system comprising a modification package according to claim 13 further in combination with a notification apparatus module which is connectable to the existing endovascular temperature management system to receive the notification signals and to provide a display or other notification upon occurrence of said at least one event.

17. A system according to claim 16 wherein the notification apparatus hardware module comprises a visible display.

18. A system according to claim 16 wherein the notification apparatus module comprises an audible alarm.

19. A system according to claim 16 wherein the notification apparatus module comprises a visible display and an audible alarm.

20. A system according to claim 17 wherein the visible display comprises a variable indicator that shows real time variation in blood flow rate.

21. A system according to claim 17 wherein the visible display comprises a visual indicator of when said at least one event is occurring.

22. A system according to claim 21 wherein the visual indicator comprises one or more light emitters.

23. A system according to claim 17 wherein the notification apparatus module provides a) a first notification indicating the resumption or continuation of effective spontaneous circulation; b) a second notification indicating the cessation of absence of effective spontaneous circulation, c) a third notification indicating when spontaneous or cardiac-compression generated circulation is occurring but is failing to generate minimum effective blood flow and d) a fourth notification indicating when spontaneous or cardiac-compression-generated circulation is occurring and is generating at least minimum effective blood flow.

24. A system comprising:
a heat exchange catheter having a heat exchange surface that is insertable into subject's vasculature;
a programmable controller;
apparatus for circulating heat exchange fluid through the heat exchange catheter while inserted in the subject's vasculature such that heat will be exchanged across the heat exchange surface between heat exchange fluid being circulated through the heat exchange catheter and blood that flows through the subject's vasculature in heat exchange proximity to the heat exchange surface;
one or more sensors for measuring a rate at which heat is being exchanged between heat exchange fluid being circulated through the heat exchange catheter and blood flowing through the subject's vasculature in heat exchange proximity to the heat exchange surface; and
wherein the controller receives signals from said one or more sensors and is programmed to use those received signals to determine a rate, if any, at which heat is being exchanged across the heat exchange surface and to ascertain whether the determined rate, if any, is indicative of an occurrence of at least one event selected from: a) resumption or continuation of effective spontaneous circulation; b) cessation or of absence of effective spontaneous circulation, c) the occurrence of spontaneous or cardiac-compression-generated circulation that is below a minimum effective blood flow rate and d) the occurrence of spontaneous or cardiac-compression-generated circulation that is at or above a minimum effective blood flow rate;
wherein, when the system is being used in a subject who lacks effective spontaneous circulation and is receiving cardiac compressions, the system determines, the rate, if any, at which heat is being exchanged across the heat exchange surface while cardiac compressions are ongoing and determines while the cardiac compressions are ongoing whether the determined rate, if any, indicates that the cardiac compressions are generating circulation that is above or below a minimum effective blood flow rate.

25. A modification package for modifying an existing endovascular temperature management system which comprises: a) apparatus for recirculating heat exchange fluid through a heat exchange catheter that is positionable within a subject's vasculature such that heat will be exchanged, across a heat exchange surface of the catheter, between heat exchange fluid being circulated through the heat exchange catheter and blood that flows through the subject's vasculature in heat exchange proximity to the heat exchange surface, b) a programmable controller programmed to control operation of the system so as to adjust or maintain a desired subject body temperature and c) sensors useable for measuring the temperature of heat exchange fluid entering the catheter and the temperature of heat exchange fluid exiting the catheter and to generate signals based on those measured temperatures:
wherein, the modification package comprises executable code stored on a storage medium and deliverable to the controller to program the controller to use signals received from said sensors to determine the occurrence of at least one event selected from: resumption or continuation of effective spontaneous circulation; cessation or absence of effective spontaneous circulation, the occurrence of spontaneous or cardiac-compression-generated circulation that is below a minimum effective blood flow rate; and the occurrence of spontaneous or cardiac-compression generated circulation that is at or above a minimum effective blood flow rate;
wherein the executable code programs the controller such that, when the endovascular temperature management system is being used in a subject who lacks effective spontaneous circulation and is receiving cardiac compressions, the controller uses said signals received from said sensors to determine while the cardiac compressions are ongoing, whether the cardiac compressions are generating circulation that is above or below a minimum effective blood flow rate.

* * * * *

UNITED STATES PATENT AND TRADEMARK OFFICE
CERTIFICATE OF CORRECTION

PATENT NO. : 10,595,791 B2  
APPLICATION NO. : 14/639816  
DATED : March 24, 2020  
INVENTOR(S) : Qing Tan and Gary A. Freeman Page 1 of 1

It is certified that error appears in the above-identified patent and that said Letters Patent is hereby corrected as shown below:

In the Claims

Column 9, Line 47, Claim 1, delete "cessation or of absence" and insert -- cessation of absence --

Column 10, Lines 16-17, Claim 9, delete "cessation or absence" and insert -- cessation of absence --

Column 10, Lines 53-54, Claim 12, delete "cessation or absence" and insert -- cessation of absence --

Column 10, Line 58, Claim 12, delete "cardiac-compression generated" and insert -- cardiac-compression-generated --

Column 11, Lines 42-43, Claim 23, delete "cardiac-compression generated" and insert -- cardiac-compression-generated --

Column 12, Line 8, Claim 24, delete "cessation or of absence" and insert -- cessation of absence --

Column 12, Line 18 (approx.), Claim 24, delete "determines," and insert -- determines --

Column 12, Lines 47-48 (approx.), Claim 25, delete "cessation or absence" and insert -- cessation of absence --

Column 12, Line 52 (approx.), Claim 25, delete "cardiac-compression generated" and insert -- cardiac-compression-generated --

Signed and Sealed this  
Fourth Day of May, 2021

Drew Hirshfeld  
*Performing the Functions and Duties of the*  
*Under Secretary of Commerce for Intellectual Property and*  
*Director of the United States Patent and Trademark Office*